United States Patent [19]

Bantz

[11] Patent Number: 4,594,897
[45] Date of Patent: Jun. 17, 1986

[54] INSPECTION OF THE INTERNAL PORTION OF OBJECTS USING ULTRASONICS

[75] Inventor: Walter J. Bantz, Coopersburg, Pa.

[73] Assignee: Bethlehem Steel Corporation, Bethlehem, Pa.

[21] Appl. No.: 574,327

[22] Filed: Jan. 27, 1984

[51] Int. Cl.$^4$ ............................................. G01N 29/04
[52] U.S. Cl. ........................................ 73/600; 73/643; 73/644; 310/336
[58] Field of Search ................. 73/644, 599, 600, 643; 310/336

[56] References Cited

U.S. PATENT DOCUMENTS

| 3,512,400 | 5/1970 | Lynnworth | 73/599 |
| 3,850,027 | 11/1974 | Nakanishi et al. | 73/600 |
| 3,928,777 | 12/1975 | Massa | 310/334 |
| 4,153,894 | 5/1979 | Alphonse et al. | 73/644 |
| 4,333,028 | 6/1982 | Panton | 310/335 |
| 4,366,712 | 1/1983 | Bathmann et al. | 73/599 |
| 4,378,699 | 12/1983 | Wickramasinghe | 73/644 |

OTHER PUBLICATIONS

"Use of Piezoelectric Transducers for Contactless Ultrasonic Product Inspection", Zaklyukoyskii et al, *Defektoskopiya*, No. 3, pp. 28–34, Mar. 1978, Translated 1978 by Plenum Publishing Corp.

*Primary Examiner*—Howard A. Birmiel
*Attorney, Agent, or Firm*—William B. Noll

[57] ABSTRACT

A transducer assembly and a system application wherein said transducer assembly may be used in the inspection of iron, steel, aluminum, as well as plastic materials as a homogeneous object in the form of a sheet, slab or bloom. Inspection is through use of ultrasonic acoustic energy propagated through ambient air. A coupling medium in the form of matching layers efficiently couple the transducer assembly to the ambient air.

26 Claims, 8 Drawing Figures

INSPECTION OF THE INTERNAL PORTION OF OBJECTS USING ULTRASONICS

TECHNICAL FIELD

The invention relates to an apparatus for and method of inspection of the internal portion of an object using ultrasonic techniques and an air medium to conduct ultrasonic energy to and receive emitted energy from the object being inspected. Although not limited thereto the invention may be used in the steel industry for detection of the presence and location of an imperfection in the internal portion of objects as well as to measure properties thereof.

BACKGROUND ART

It is known in the prior art that ultrasonic energy may be coupled by liquid coupling techniques to the surface of an object being tested. This conventional type coupling, however, generally is considered not to be practical under circumstances that the object under test, such as a bloom or slab is at a high temperature.

It is also known in the prior art that electromagnetic acoustic (EMAT) and laser pulse generation techniques are two methods of noncontact generation and reception of ultrasound. These noncontact techniques are not without their drawbacks. For example, the EMAT method requires proximity of the transducer to the material being tested. The laser method requires high power and a confined beam to generate ultrasound. Further, both of these methods have poor sensitivity as receivers of ultrasound.

The use of air as a coupling medium has been discussed in several papers. One paper, entitled "Use of Piezoelectric Transducers for Contactless Ultrasonic Product Inspection", by V. I. Zaklyukoyskii and G. T. Kartsev, describes the use of a piezoelectric transducer for contactless ultrasonic inspection of objects of various materials and the use of matching components for coupling ultrasound into air. According to this paper the ultrasonic transducer uses a piezoelectric layer operating at half-wave resonance and one or more matching layers operating at quarter-wave resonance.

The invention distinguishes from the disclosure of the paper discussed above in that the ultrasonic transducer configuration of the invention uses a piezoelectric layer which operates at other than half-wave resonance and a first matching layer of a coupling medium which operates at other than quarter-wave resonance. Only a second matching layer of the coupling medium operates in quarter-wave resonance at the operating frequency determined by the composite of the transducer-first layer thickness and acoustic impedance. The net result is that the ultrasonic transducer of the invention has much higher efficiency than that described in the paper. The higher efficiency is supported by results of experiments in the aforementioned paper, which describe the capability of penetrating 3 cm of steel with a 10 to 1 signal to noise ratio (voltage or power not specified). According to the present invention penetration of steel of 10 cm and thicker, with a signal to noise ratio of 60 to 1 voltage (3600 to 1 power) has been obtained. In addition, the paper describes an operating frequency of 40–50 kHz. This frequency requires the use of acoustic waveguides to transmit the ultrasound to and from the test sample, and acoustic shields to prevent sound from leaking around the test sample. According to the invention, considerably higher efficiencies have been achieved with an operating frequency of 250 kHz, and even higher. This operation obviates the need for waveguides and shields.

Two other papers have some degree of relevance to the invention for reason of a reference to excitation of Lamb waves using airborne ultrasound. These papers are entitled "Metal Plate Testing Using Airborne Ultrasound", by M. Luukala and P. Merilainen and "Ultrasonics Plate Waves in Paper", by C. C. Habeger, R. W. Mann and G. A. Baum. According to the Luukala et al paper, the method of excitation and detection is carried out through use of well-known capacitive transmitters and receivers having, typically, an efficiency of about 0.2%. According to the Habeger et al paper, the method of excitation and detection is carried out with a transducer, such as a film transducer wherein the piezoelectric action is imparted to the film by repeatedly charging and discharging the capacitance of the film. The efficiency achieved by practice of the Habeger et al teaching is not disclosed, but there is no reason to believe that the efficiency achieved would be any greater than the efficiency achieved by the Luukala et al teaching.

The present invention, in contrast, provides for an efficiency of 7.0% or more using an ultrasonic transducer together with a piezoelectric layer and coupling medium, as generally described above and more particularly described below. The present invention, also, obviates various technical complexities which oftentimes are encountered with a laser-type system. In addition, the costs are considerably less. Further, the use of air to couple ultrasound poses no danger to an operator as with use of laser pulse ultrasound generation systems.

SUMMARY OF THE INVENTION

The invention relates to apparatus and a method for noncontact ultrasonic inspection of the internal portions of an object which may be at an elevated temperature to detect a lack of homogeneity in the object under test. The apparatus and method of inspection utilizes air to conduct the ultrasonic energy to and receive ultrasonic vibrations emitted from the object. According to the invention ambient air is used to conduct ultrasonic energy. As such, the assembly including the transducer, piezoelectric layer and coupling medium may be spaced an inch or more from the object under test and, because of the manner of coupling the energy, a high sensitivity in reception is achieved even though losses in coupling acoustic energy at the air-object boundary may be considerable.

The system generally includes a source of an oscillatory burst of energy at the frequency of an ultrasonic transducer, a piezoelectric layer for transforming electrical energy to ultrasonic energy, and vice versa, a coupling medium in the form of matching layers to achieve high efficiency coupling of the ultrasound to and from ultrasonic transducers into air, and a detector for processing the signal thereby detecting an imperfection or measuring a property of the internal portion of an object or incremental portions of an object moved to a testing location.

The detector may be responsive to the amplitude of received ultrasound, after it shall have been transformed to electrical energy and/or it may be a viewing instrumentality, likewise responsive to the amplitude of the electrical energy.

Various types of waves of ultrasonic waves may be developed by orientation of the transducer assembly and the direction in which the ultrasound propagates in the coupling medium. To this end, if the direction in which the ultrasound propagates is substantially perpendicular to the surface of the object a longitudinal wave will propagate within the object. On the other hand, if the direction of propagation makes a slight acute angle a shear wave will propagate within the object, and as the angle is increased further, a surface wave will propagate within the object. Other types of waves, for example, Lamb waves can be generated in thin objects.

A system application of the invention may include a pair of transducer assemblies, one comprising a transmit transducer and the other comprising a receive transducer for receipt of ultrasonic energy emitted from the object.

In another system application of the invention, there may be a single transmit-receive transducer for detection of imperfections or the measurement of the internal portion of objects using a so-called "pulse-echo" detection mode. In this mode of operation, the transmit pulse should be of a duration controlled by the time to receive the pulse to be detected, and which pulse includes the information to be displayed. An amplifier or amplifiers may be used in the system applications, as may be necessary.

In another system application of the invention, the ultrasound propagated from one transducer assembly toward an object or propagated from the object for receipt by the other transducer assembly may each be focused by a reflective surface for reduction in the diameter of the sound beam.

An important aspect of the invention is in the coupling medium for achieving the high efficiency coupling of ultrasound to and from ultrasonic transducers into air. The coupling medium includes matching layers formed by specific lamina compositions and thicknesses, and which lamina or matching layers are located in predetermined position relative both to the piezoelectric layer of the transducer assembly and air.

In the broadest definition of a system application, the invention is described by a receiver transducer spaced from an object under test for receipt of ultrasonic energy emitted from the object into air, a detector for detecting an attenuation in the ultrasonic energy and transduced electrical energy indicative of an imperfection in the object under test, a coupling medium forming a part of the transducer assembly for receiving ultrasonic energy, and a source of ultrasonic energy which is directed toward the object which then is received by the receiver transducer. The source of ultrasonic energy may comprise a second transducer assembly for transmitting the ultrasonic energy similarly spaced from the object by an air gap, and similarly including a coupling medium. Each coupling medium includes matching layers to achieve a high efficiency coupling of ultrasonic energy into air. The source of ultrasonic energy may be located either on the same side or on the opposite side of the object under test, and the transducer assemblies may comprise a single transducer having capability of operation in a pulse-echo mode of operation.

The invention is also directed to a transducer assembly for use in a detection system formed by a transducer and a piezoelectric layer together with a coupling medium for achieving a high efficiency coupling of ultrasonic energy into air.

Other aspects, definitions and features of the invention will become clear as the description to be considered in conjunction with the drawing continues.

BEST MODE FOR CARRYING OUT THE INVENTION

A system and apparatus for inspection of a homogeneous media to detect imperfections and/or measure the properties of the internal portion of the object may be seen in the Figures. The media to be tested may be comprised of iron, steel, aluminum or of plastic, to name a few common materials, and, for example, may be in the form of a sheet, slab or bloom of material. The system and apparatus may be used to detect the presence and location of an imperfection in a sheet or, for example, a shrinkage cavity (pipe) in a hot bloom or slab. All in all, the system and apparatus through detection of the presence and location of any imperfection will provide better yield and quality of product.

Figure 1:
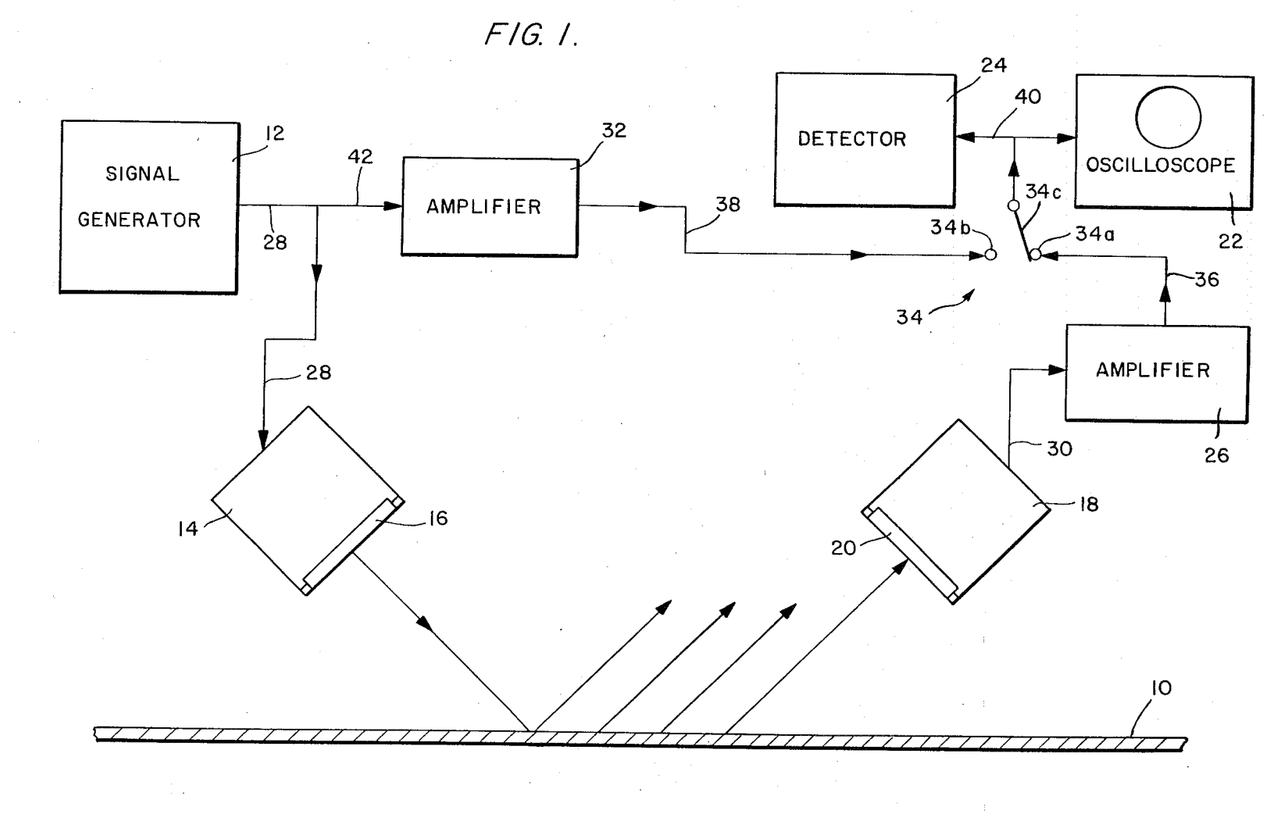
FIG. 1 is a schematic presentation of an apparatus and system for air-coupled ultrasonic inspection of the presence and location of an imperfection in the internal portion of a sheet.

Referring to FIG. 1, a sheet 10 is illustrated in position for test. Testing may be carried out on individual sheets of material, but preferably the sheet will be a continuous sheet moved by structure (not shown) along a conveyor path through a testing location whereby each increment of the length of the sheet is subject to test.

Inspection at a testing station is carried out by an electrical system including a signal generator 12, a transducer 14 including a layer of piezoelectric material for transforming electrical energy to ultrasonic energy, and a coupling medium 16 for efficient coupling of ultrasound into air. The transducer, piezoelectric layer and coupling medium, itself including matching layers, heretofore has been referred to as a "transducer assembly". The signal generator functions to produce an oscillatory burst of energy over a relatively short time duration at the resonant frequency of the transducer assembly.

The signal generator may be a Velonex Model 570 with Model 350-12 Plug-In. The layer of piezoelectric material of the transducer assembly may comprise a lead zironate titanate (for example, a Vernitron Piezoelectric Division, designation PZT-4 or PZT-5H) having a thickness $T(t)$, longitudinal acoustic velocity $V(t)$ and acoustic impedance $Z(t)$. A successful test has been carried out with such a piezoelectric layer and matching layers, to be discussed; with an oscillatory burst of energy at a frequency of 250 KHz over a 20 μsec duration.

The ultrasound propagates in a direction which essentially is normal to the surface of the coupling medium 16 thereby to strike sheet 10 at an incident angle α. As is well known, at certain values of α, so-called "Lamb wave" modes will be generated and propagated in the sheet. The preferred magnitude of the angle of incidence is dependent upon several factors. These factors include the thickness of the material, in this instance the sheet under inspection, the frequency of operation and the desired wave mode generated in the sheet. The incident angle is an angle referenced to a path of propagation of ultrasound which is perpendicular to the surface of the object, or at 0°. The Lamb wave will propagate along the sheet and radiate from the sheet as an ultrasonic vibration at the same angle toward a receiver transducer. More particularly, the Lamb wave propagates along the sheet, emitting an amount of ultrasonic energy as it propagates.

A second transducer assembly, like the transducer assembly first-mentioned is located in a position that the ultrasonic energy emitted from the sheet is directed substantially normal to its receiving surface. More particularly, the second transducer assembly includes a transducer 18 including a layer of piezoelectric material to transform the airborne ultrasound into electrical energy for detection and a coupling medium 20 for efficient coupling of the ultrasound between the ultrasonic transducer and air.

The ultrasound moving toward sheet 10 is depicted by a single directional arrow, whereas, the ultrasonic vibrations emitted from the sheet as the wave propagates along the sheet is depicted by a plurality of directional arrows.

The ultrasonic energy that is transformed to electrical energy is displayed on an oscilloscope 22 and/or detected by a detector 24. The ultrasonic energy coupled between the transducer assemblies will be attenuated by losses at the air-object boundaries. However, the efficiency of the overall system of operation is improved, possibly several hundred times, over conventional transducer assemblies thereby to permit sensitive inspection of objects even though these losses may be considerable. Should an imperfection be present in the sheet between the point of entry of sound and the point at which the sound vibrations are emitted, the receiving transducer will respond to an attenuation that may be anticipated. This decrease in sound amplitude indicative of the imperfections, is displayed and/or detected. An amplifier 26 may be provided to amplify the electrical signal.

The oscilloscope 22 may be Tektronix Model 7904 with Model 7A22 Vertical Amplifier and Model 71370, 71371 Plug-In. The amplifier 26 may be a Panametrics Ultrasonic Preamplifier.

While the transducer assemblies are illustrated on the same side of sheet 10, the transducer assemblies, equally as well, may be located on opposite sides of the sheet. This arrangement of structure will be appreciated from forms of system applications to be discussed below.

Suitable electric connectors are used to connect the components of the system. To this end, a connector 28 connects signal generator 12 and transducer 14 of the first transducer assembly, connector 30 connects transducer 18 of the second transducer assembly and amplifier 26.

System operation may be carried out following the mode of operation previously discussed, characterized as a "through transmission" mode, or the mode of operation may be one which is carried out in response to ultrasound which is reflected to transducer 14 of the first transducer assembly by an imperfection that reflects ultrasonic energy. In this instance transducer 14 functions as both a transmitter and receiver transducer for ultrasound. Therefore, in this operation the duration of the burst of energy must be timed to provide a quiescent period of transmission during which the ultrasound reflected back to the receiver transducer may be received. The duration of the transmit pulse principally will be determined by the sound velocities in both air and sheet material and the distance between the sheet material and the dual capability transducer. Thus, for example, a transmit pulse may continue during a duration of time, and repeat for periods of similar duration at a predetermined frequency thereby to receive reflected ultrasonic energy during each period between bursts. These periods may be determined relatively easily. This mode of operation may be characterized as a "pulse-echo" mode.

The ultrasound which is reflected likewise is attenuated by the air medium and the sheet medium. An amplifier 32 provides the function of amplifier 26 in the pulse-echo mode of operation. The amplifier, further, may be of the type previously discussed.

A switch 34 is included in the system to set the mode of operation that is desired. A connector 36 connects amplifier 26 to stationary contact 34a of switch 34, and a connector 38 connects amplifier 32 to stationary contact 34b of the switch. A connector 40 is connected to the movable contact 34c, and connector 42 connects amplifier 32 to receive transducer 14. FIG. 1 illustrates the system in the through transmission mode of operation.

Figure 5:
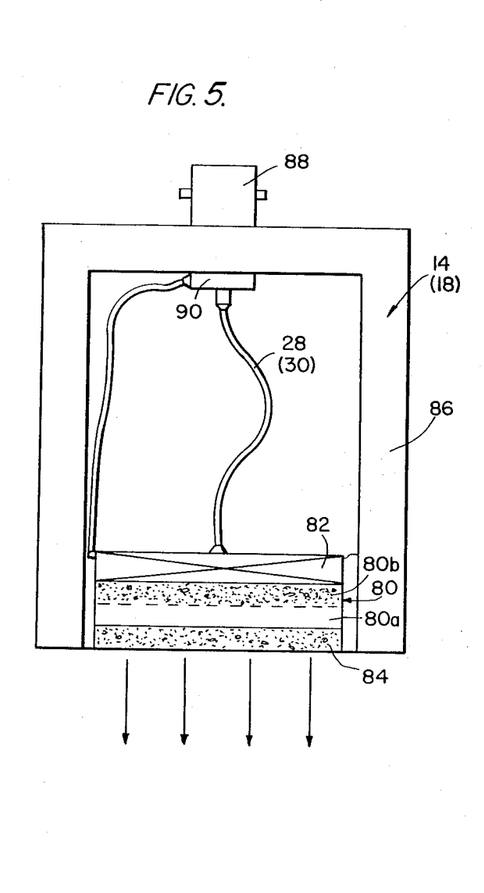
FIG. 5 is a schematic presentation of a transducer assembly.

An important aspect of the invention concerns the coupling media 16, 20 of each transducer assembly. Referring to FIG. 5, the coupling media includes a first matching layer 80 of an acoustic impedance $Z(1)$ between about $6 \times 10^6$ and $8 \times 10^6$ Pascal-seconds-meter (PaS/M), a thickness $T(1)$ and a longitudinally velocity $V(1)$. The first matching layer is disposed adjacent a layer 82 of piezoelectric material. The first matching layer, as described and as will be hereinafter discussed, is an ideal and may be constituted by a pair of layers 80a, 80b. A second matching layer 84 is disposed on the opposite side of the first matching layer. The second matching layer which provides an interface with the air has an acoustic impedance $Z(2)$ of less than $5 \times 10^5$ PaS/M, a thickness $T(2)$ and a longitudinal velocity $V(2)$. The transducers of the transducer assemblies include a housing 86 for supporting the piezoelectric layer 82 and the matching layers 80, 84 of the coupling media 16(20), a connector 88 for electrical connection to external equipment and a terminal 90 for connector 28(30).

The frequency of operation and thickness relationship of the layer 82 of piezoelectric material and the first matching layer 80 are determined by a theoretical (approximate) formula:

$$\frac{Z(t)}{Z(1)} = \tan \phi (1) \frac{\sin \phi(t) - 2B(1 - \cos \phi(t))}{\cos \phi(t) - B \sin \phi(t)}$$

where:

$$\phi(a) = 2 \times \pi \times f \times T(a)$$

f is the frequency of overall transducer operation $$B \text{ is } \frac{2 \times k^2 \times f_0}{\pi \times f}$$

$$f_0 \text{ is } \frac{V(t)}{2T(t)}$$

k is the electromechanical coupling coefficient of the piezoelectric materials and a is simply an index (here 1 or t).

In the determination of operating frequency it may be best to construct two identical piezoelectrical-first layer transducers (80a, 80b) based on equation (1), and measure peak transmission frequency through air. There are two resonant frequencies. One resonant frequency is below the self-resonant frequency of the transducer, and the other resonant frequency is above the self-resonant frequency. The lower frequency may be preferred since it usually exhibits stronger transmission. The second matching layer 84 is selected such that $$f = \frac{V(2)}{4 \times T(2)} \text{ (a quarter wave resonance)} \quad (2)$$

It was previously indicated that the first matching layer 80 (ideal) has an acoustic impedance of about $6 \times 10^6$ PaS/M. Materials displaying this level of acoustic impedance normally are not readily available. Accordingly, an important aspect of the invention is to synthesize the first matching layer, having a desired thickness, with a pair of layers 80a, 80b. One of these layers will have an acoustic impedance below that desired, while the other layer will have an acoustic impedance above that desired. The acoustic impedances are represented as Z(11) and Z(12), respectively. Materials having an acoustic impedance of Z(11) and Z(12) will be readily available.

Given a desired acoustic impedance, Z(1), the ratio of thickness to longitudinal velocity, T(1)/V(1), and the known acoustic impedances, Z(11) and Z(12), it is possible to determine the frequency at which the desired first layer would be quarter wave resonant using $$f_q = \frac{V(1)}{4 \times T(1)}$$

The ratio T(11)/V(11) and T(12)/V(12) may also be determined by these formulas:

$$\tan \phi(11) = \frac{Z(1)^2 - Z(11)^2}{Z(12)^2 - Z(1)^2} \quad (3)$$

$$\tan \phi(12) = \sqrt{\frac{Z(11)}{Z(12) \times \tan \phi(11)}} \quad (4)$$

where $$\phi(a) = \frac{2 \times f_q \times T(a)}{V(a)}$$

If the velocity of the longitudinal acoustic wave is known for each material, T(11) and T(12) may be calculated.

Figure 6:
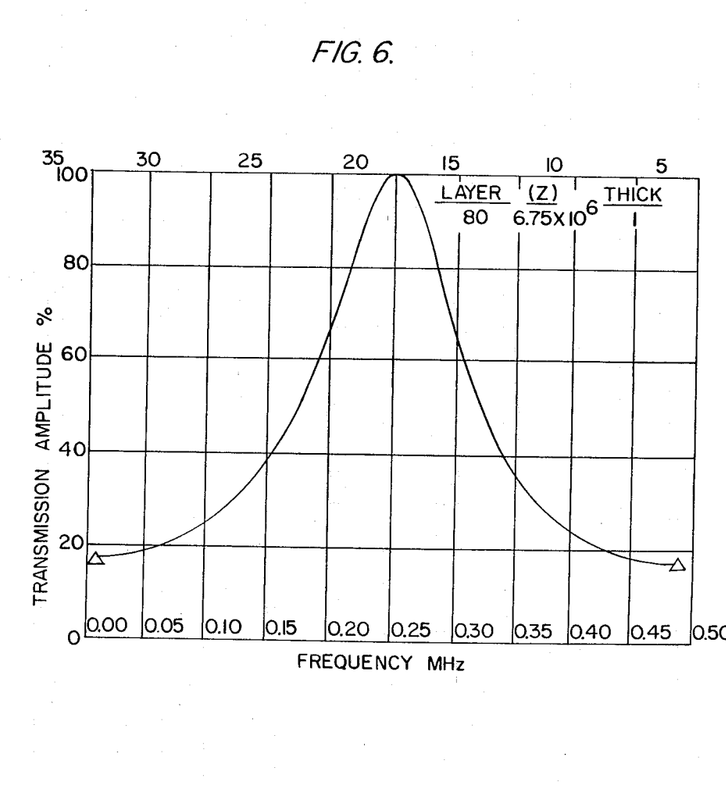
FIGS. 6–8 are graphs illustrating the transmission coefficient (percentage) as a function of frequency.
Figure 7:
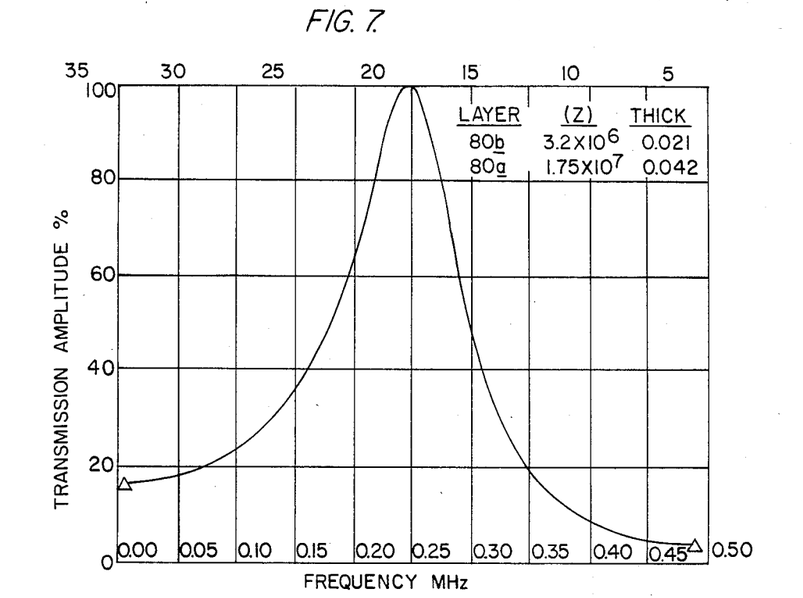
Figure 8:
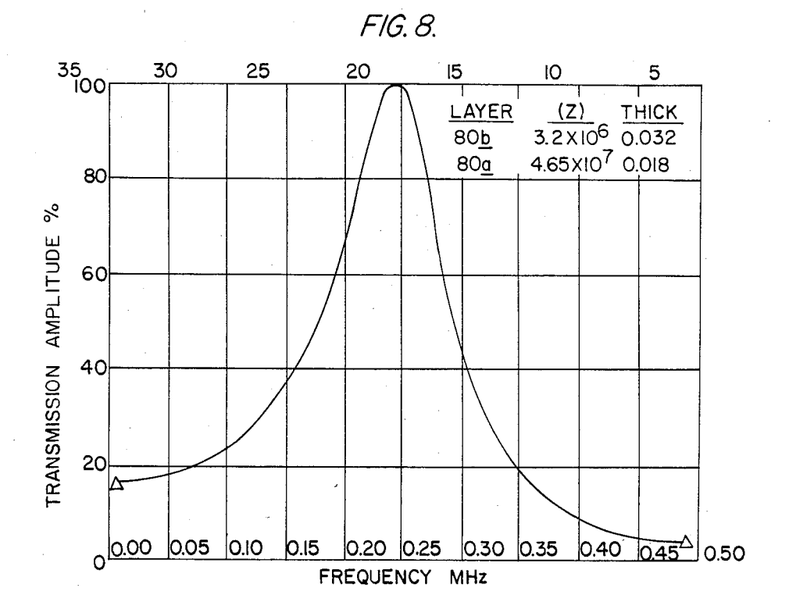

A practical example of the above discussion may be appreciated from the discussion to follow and FIGS. 6–8. As will be seen, noting, also, FIGS. 6–8, the determination provides a good approximation of the acoustic properties of the desired layer for frequencies equal to and below quarter wave resonance of the desired layer. Referring to the Figures, there is illustrated a curve representing transmission from a medium of acoustic impedance of $3.1 \times 10^7$ PaS/M, the piezoelectric layer 82 (PZT-4), to a medium of acoustic impedance of $1.47 \times 10^6$ PaS/M. The last-mentioned medium, closely representing the material of the second matching layer 84 in quarter wave resonance with air backing in acoustic impedance, is water.

Referring to FIG. 6, there is illustrated the transmission coefficient as a function of frequency for a conventional quarter wave matching layer having an acoustic impedance of $6.75 \times 10^6$ PaS/M. This value of acoustic impedance is within the range of acoustic impedances previously discussed for the first matching layer 80. FIG. 7 illustrates an equivalent for use as a first matching layer. The equivalent includes a pair of layers, 80a, 80b. The layer 80a is comprised of aluminum having an acoustic impedance of $1.75 \times 10^7$ PaS/M, and the layer 80b is comprised of plexiglass having an acoustic impedance of $3.2 \times 10^6$ PaS/M. The thickness of the aluminum and plexiglass layers, expressed in quarter wavelength equivalents, are 0.2250 and 0.2940, respectively. FIG. 8 illustrates another equivalent for use as a first matching layer. The equivalent likewise includes a pair of layers 80a, 80b. The layer 80a is comprised of steel having an acoustic impedance of $4.65 \times 10^7$ PaS/M, and the layer 80b is comprised of plexiglass having an acoustic impedance of $3.2 \times 10^6$ PaS/M. The thickness of the steel and plexiglass, expressed in quarter wavelength equivalents, are 0.0820 and 0.3120, respectively.

The material having the acoustic impedance Z(11) is the layer closest to the high impedance material which, in this description, is the layer 82 of the piezoelectric material.

In the system application of the invention of FIG. 1, the apparatus is as described and the operation is carried out according to the following specifications:

| | |
|---|---|
| Operating frequency | 250 KHz |
| Sheet 10 | 0.1 inch steel |
| Angle α | 8° (the angle is increased as the thickness of the sheet is decreased. For example, an angle of 19° may be used in testing a sheet of steel having a thickness of 0.020 in) |
| Piezoelectric material | PZT-4, 0.25 inch thickness, and 1.5 inch diameter |
| Coupling medium | (from the piezoelectric material toward the sheet) |
| | plexiglass   0.021 inch |
| | aluminum    0.042 inch |
| | balsa wood  0.050 inch |
| | (across grain) |

The system application of FIG. 1 may be used in the detection of laminations or gouges in the plane of the sheet. The system, as described, utilizes ambient air to transmit ultrasound sound to, and receive ultrasonic vibrations emitted from the object under test. This system, as discussed, utilizes a unique design of coupling medium which efficiently couples the ultrasound to ambient air. To this end, the coupling medium including its matching layers overcomes the great losses normally encountered in coupling acoustic energy from solids to gases, and provides a high efficiency coupling of ultrasound to and from ultrasonic transducers into air. Since the efficiency is improved several hundred times over conventional transducers, a sensitive inspection of objects is possible even though there still is considerable loss at the air-object boundary. The frequency of operation is also significant in that the high frequency permits detection of relatively small defects, a degree of detection not possible when operation is carried out at frequencies of about 20-50 KHz.

Figure 2:
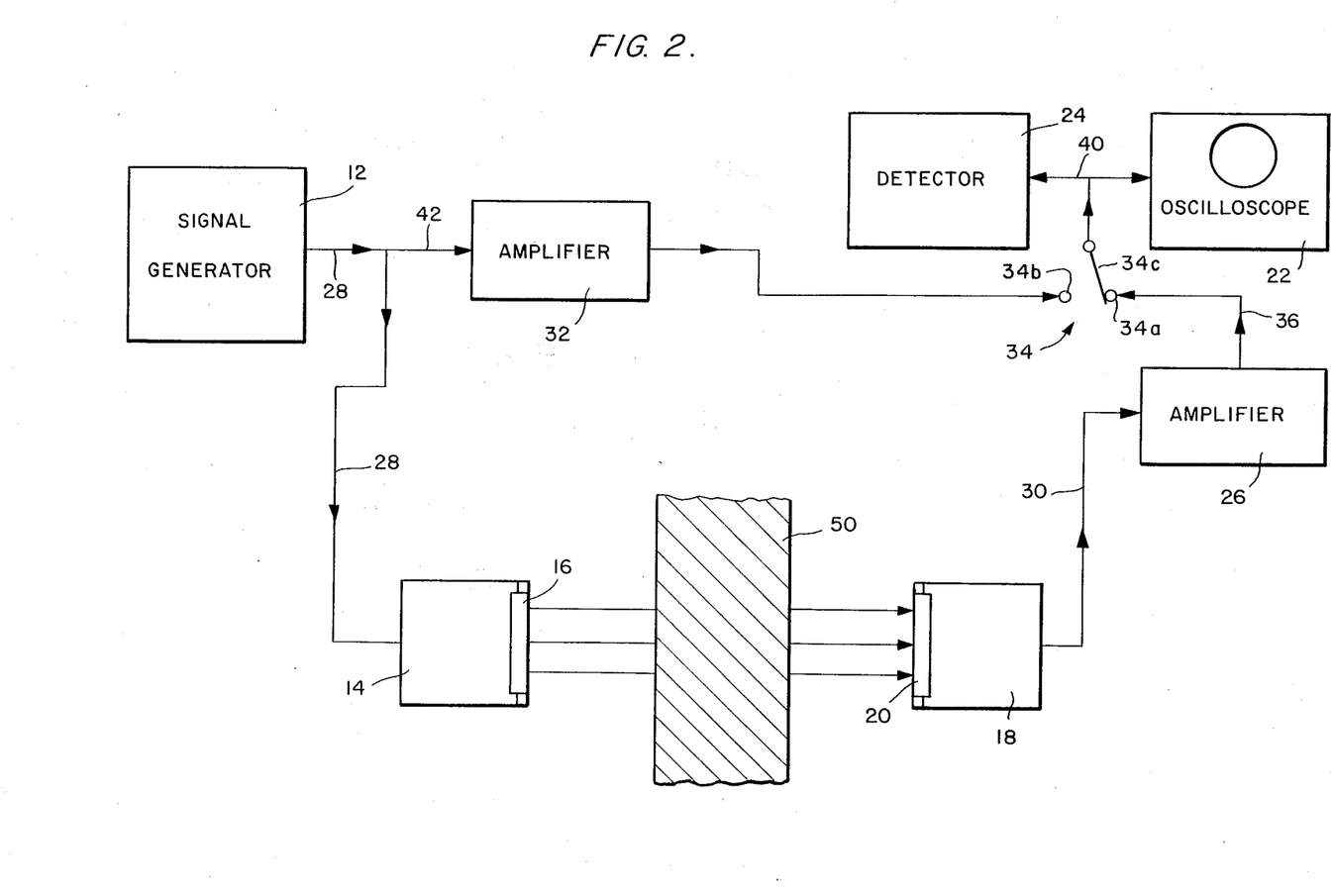
FIG. 2 is a schematic presentation like FIG. 1 for air-coupled ultrasonic inspection of a slab.

FIG. 2 illustrates the system application like that of FIG. 1 with the transducers 14, 18 of the transducer assemblies arranged on opposite sides of an object 50 under test. The object may be a slab of substantially any media, such as iron, steel, aluminum, and plastic. Generally, a slab is considered to have a width of about two or more times that of the thickness which, in this form of the invention, may be 4 inches or more. The slab may be conveyed by any form conveying apparatus capable of handling the object, which may be in a hot condition, and moving the object to and through the location for inspection and detection.

In the form of the invention of FIG. 2, the operation may be carried out according to the following specifications:

| | |
|---|---|
| Operating frequency | 250 KHz |
| Slab 50 | 4 inch thick (homogeneous media) |
| Angle α | 0° (longitudinal wave) |
| | 4° (45° shear wave) |
| Piezoelectric material | PZT-5H, 0.25 inch thickness, and 1.5 inch diameter |
| Coupling medium | (from the piezoelectric material toward the slab) |
| | plexiglass 0.032 inch |
| | steel 0.018 inch |
| | polystyrene foam 0.040 inch |

This operation may be carried out to detect voids or inclusions in the object under test. In this test, the ultrasonic waves propagate through the thickness of the object and any imperfection in the path of the ultrasonic waves attenuates the propagating wave to produce a reflected wave. Detection may be carried out in a manner as previously discussed. In addition, using only the transducer 14 of the first transducer assembly, the thickness of the object under test may be measured by detecting the wave reflected from the surface of the object closer to the transducer and then, measuring the time of arrival of the wave reflected from the other surface of that object.

The system application of FIG. 2 is carried out with the coupling medium including a layer of polyethylene foam, layer 84, in replacement for the layer of balsa wood. This replacement has led to a somewhat improved performance in testing. Similar improvement has been realized in the replacement of the aluminum-plexiglass layer, layers 80a, 80b, with a steel-plexiglass layer.

Figure 3:
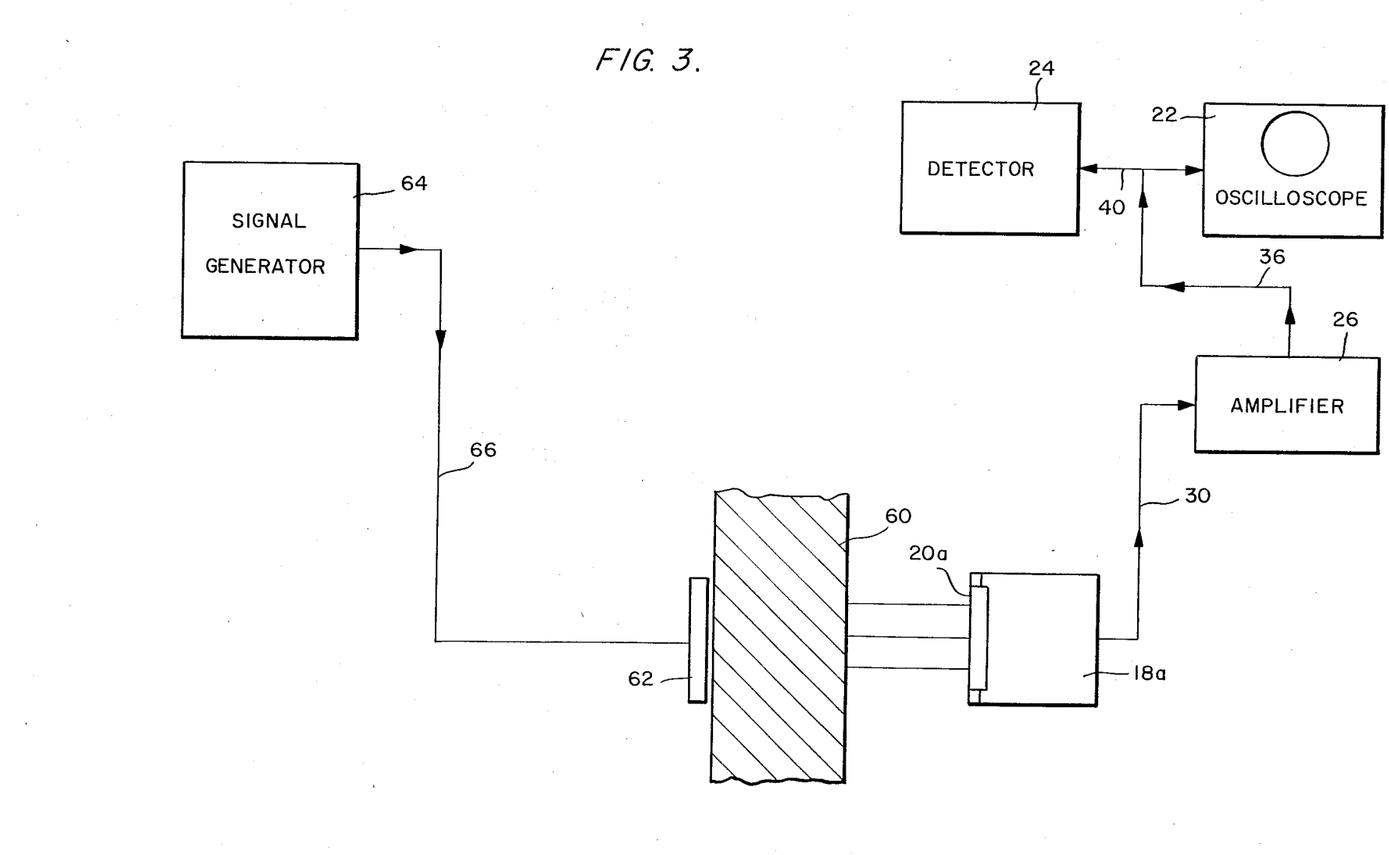
FIG. 3 is a schematic presentation like FIG. 2 wherein the apparatus and system includes an electromagnetic acoustic transducer.

FIG. 3 illustrates another system application which may be especially advantageous for use in the inspection of hot objects. Under these circumstances, the proximity of the transducer assembly including the coupling medium for transmitting the ultrasound to the hot surface of the material would render the layer 84, either balsa wood or plastic foam, susceptible to destruction. The close proximity requirement for the transmitting transducer is founded upon a known rapid attenuation of high intensity ultrasound (approximately 1w/cm²) due to nonlinear properties of air. This requires the transmitting transducer to be placed close (one inch or less for operating frequencies of 250 KHz) to the surface of the test object. Referring to FIG. 3, a slab 60 which may be a continuous slab of metal, such as that previously described is supported for movement through a testing location. Inspection at the testing location is carried out by an electrical system generally like the system previously discussed except for the use of an electromagnetic acoustic transducer 62 (EMAT). The transducer is controlled by a signal generator 64. The coil of the exciting transducer may be formed as a flat, spiral wound coil of wire for generation of a repulsive force between the current in the coil and induced currents in the object. This system application may also use other types of excitation means, such as lasers or contact transducers with air-coupled receivers. The receiver transducer 18a and coupling medium 20a of the transducer assembly generally duplicate the structure previously discussed above. This is true, also, of the detection components of the system. As to the excitation portion of the inspection system, the signal generator has an operating frequency of from 250 to 750 KHz and is connected to transducer 62 by conductor 66. Defects, such as voids or inclusions in the slab may be detected.

Figure 4:
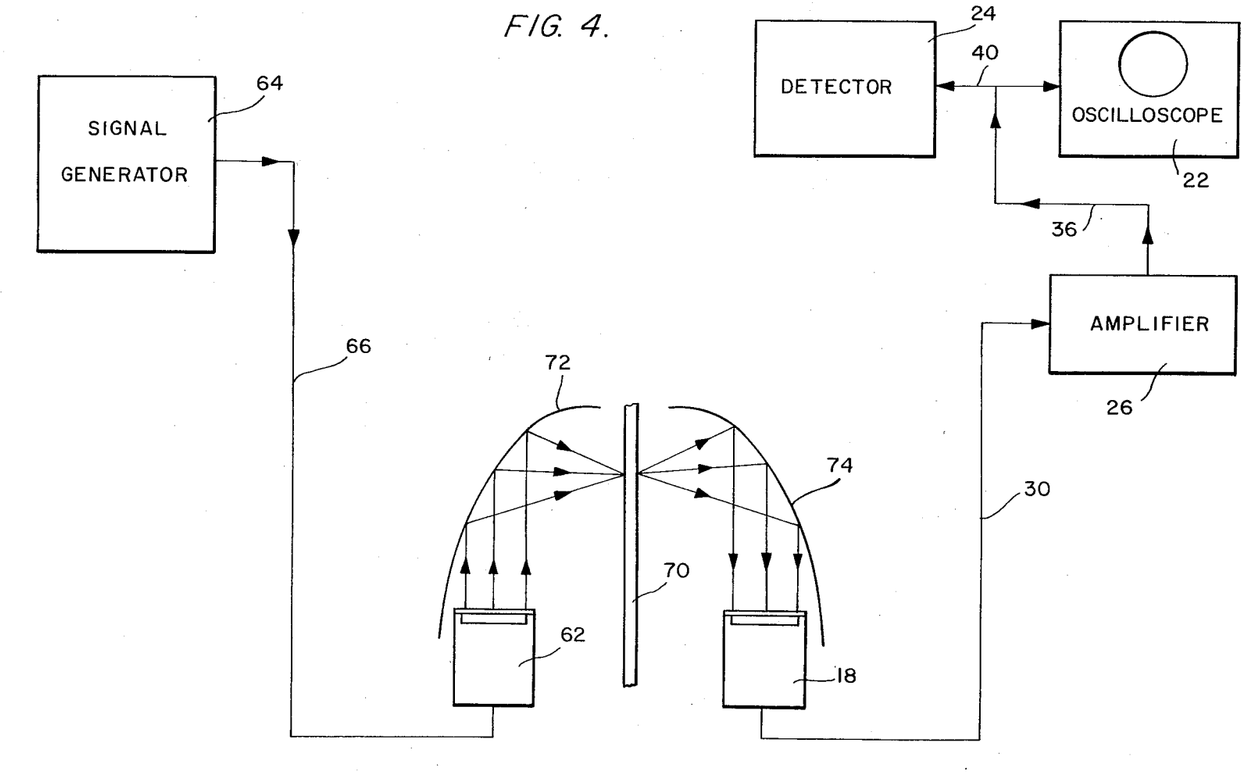
FIG. 4 is a schematic presentation like that of the foregoing Figures for air-coupled ultrasonic inspection of a sheet using a pair of reflective surfaces.

FIG. 4 illustrates a further system application and an excitation portion which generally duplicates that of FIG. 3. The major difference as illustrated in FIG. 4 relates to the use of a reflector 72 having a parabolic reflective surface for reducing the diameter of the sound beam. A similar reflector 74 picks up the airborne ultrasonic energy and directs the energy toward the receiving transducer 18. The detection components duplicate those of FIG. 3.

The frequency generator 64 operates at a frequency of 250 to 750 KHz for testing a sheet 70 of a material, such as steel, aluminum or plastic. The sheet may have a thickness of about 0.1 inch or less, and laminations in the sheet may be detected. The reflectors provide an additional advantage. To this end, the parabolic configuration permits attainment of high ultrasonic intensity near the surface of the object under test while locating the transmitter transducer at a distance from the object. This is due to the avoidance of high attenuation due to high intensities, as already mentioned, other than near the reflector focal distances. The use of a reflector may be considered in all system applications.

I claim:

1. A system for detection of imperfections and measurement of properties of the internal portion of an object including (a) a source of ultrasonic acoustic energy generating a wave mode which propogates along said object under test, (b) a receiver transducer spaced from said object and coupled by ambient air with ultrasonic vibrations emitted from said object, (c) means forming a part of said receiver transducer for matching acoustic impedance and optimizing the coupling efficiency of said emitted ultrasonic vibrations from ambient air into a piezoelectric material, said means comprised of at least first and second juxtaposed layers of material having an acoustic impedance, said second layer of material being disposed remote from said piezoelectric material having a thickness equivalent different from said first material and equal to a quarter wave-length, and (d) detector means for detecting any attenuation of the energy level of said emitted ultrasonic vibrations which characterizes the physical make-up of said object under test.

2. The system of claim 1 wherein said object is in the form of continuous body of material and including means adapted for moving continuously said object relative to said source of ultrasonic acoustic energy to provide for continuous detection and measurement.

3. The system of claim 1 wherein a first matching layer has an acoustic impedance between about $6 \times 10^6$ and $8 \times 10^6$ PaS/M, and said second matching layer has an acoustic impedance of less than $5 \times 10^5$ PaS/M, said second matching layer adjacent said ambient air having a thickness equivalent to a quarter wavelength.

4. The system of claim 3 wherein said first matching layer comprises two individual layers.

5. The system of claim 1 further including an amplifier for amplifying a level of electrical energy representative of said ultrasonic vibrations transduced by said receiver transducer.

6. The system of claim 1 further including either one or both of a detector and display responsive to said electrical energy and any change in said level.

7. The system of claim 6 including a detector.

8. The system of claim 6 including a display.

9. The system of claim 1 wherein said source of ultrasonic acoustic energy comprises a signal generator, a transmitter transducer, and means forming a part of said transmitter transducer for optimizing the coupling efficiency of said ultrasonic acoustic energy into ambient air.

10. The system of claim 9 wherein said transmitter transducer is disposed on the same side of said object as said receiver transducer.

11. The system of claim 10 wherein a surface of said transmitter transducer from which said ultrasonic energy propagates is disposed at an acute angle relative to the surface face of said object.

12. The system of claim 11 further including a switching circuit for switching said system from a through transmission mode of operation to a pulse-echo mode of operation, said switching circuit connecting said detector and display to one of said receiver transducer and transmitter transducer, respectively.

13. The system of claim 9 wherein said transmitter transducer and receiver transducer are located on opposite sides of said object.

14. The system of claim 13 wherein a surface of said transmitter transducer from which said ultrasonic acoustic energy propagates is disposed at an angle of from 0° to 90° relative to the surface of said object.

15. The system of claim 14 further including a switching circuit for switching said system from a through transmission mode of operation to a pulse-echo mode of operation, said switching circuit connecting said detector and display to one of said receiver transducer and transmitter transducer, respectively.

16. A transducer assembly for use in a system for detection of imperfections and measurement of properties of the internal portions of an object using ambient air to transmit ultrasound to, and to receive ultrasonic vibrations emitted from the object, said transducer assembly including (a) a piezoelectric material having capability of transforming oscillatory energy at a resonant frequency of the transducer assembly to ultrasonic energy and the reverse, and (b) means comprised of at least a first and a second matching layer of material juxtaposed one another forming a part of said transducer assembly, said matching layers of material each having an acoustic impedance and said second matching layer of material disposed on the side of said first matching layer further from said piezoelectric material, said second matching layer only having a thickness equivalent to a quarter wavelength or multiple thereof, said layers of material being adapted for matching acoustic impedance and optimizing the coupling efficiency of said ultrasonic energy and airborne ultrasound into and from ambient air, and said airborne ultrasound which is adapted to be emitted from said object whose internal properties are subject to test being attenuated by any imperfection of property thereby bearing a relationship to the physical make-up of said object.

17. The transducer of claim 16 wherein said layer of material closer to said piezoelectric material comprises a first matching layer having an acoustic impedance between about $6 \times 10^6$ and $8 \times 10^6$ PaS/M, and a second matching layer removed from piezoelectric material and adjacent said ambient air having an acoustic impedance of less than $5 \times 10^5$ PaS/M.

18. The transducer of claim 17 wherein said first matching layer comprises two individual layers.

26. The system of claim 1 wherein said source of acoustic energy comprises a signal generator, and an electromagnetic exciting transducer formed by a coil of wire.

19. A system for detection of imperfections and measurement of properties of the internal portion of an object including (a) a source of ultrasonic acoustic energy generating a wave mode which propogates along said object under test, (b) a receiver transducer spaced from said object and coupled by ambient air with ultrasonic vibrations emitted from said object, (c) a first matching layer including two individual layers having an acoustic impedance between about $6 \times 10^6$ and $8 \times 10^6$ PaS/M comprised of
  (1) a layer of plexiglass, and
  (2) a layer of aluminum, respectively, (d) a second matching layer disposed adjacent said ambient air having an acoustic impedance of less than $5 \times 10^5$ PaS/M, said second matching layer, further, comprised of balsa wood and having a thickness equivalent to a quarter wavelength, and wherein said first and second matching layers form a part of said receiver transducer for matching acoustic impedance and optimizing the coupling efficiency of said emitted ultrasonic vibrations from ambient air into a piezoelectric material, and (e) detector means for detecting any attenuation of the energy level of said emitted ultrasonic vibrations which characterizes the physical make-up of said object under test.

20. A system for detection of imperfections and measurement of properties of the internal portion of an object including (a) a source of ultrasonic acoustic energy generating a wave mode which propogates along said object under test, (b) a receiver transducer spaced from said object and coupled by ambient air with ultrasonic vibrations emitted from said object, (c) a first matching layer including two individual layers having an acoustic impedance between about $6 \times 10^6$ PaS/M and $8 \times 10^6$ PaS/M comprised of
  (1) a layer of plexiglass, and
  (2) a layer of steel, respectively, (d) a second matching layer disposed adjacent said ambient air having an acoustic impedance of less than $5 \times 10^5$ PaS/M, said second matching layer, further, comprised of polystrene foam and having a thickness equivalent to a quarter wavelength, and wherein said first and second matching layers form a part of said receiver transducer for matching acoustic impedance and optimizing the coupling efficiency of said emitted ultrasonic vibrations from ambient air into a piezoelectric material, and (e) detector means for detecting any attentuation of the energy level of said emitted ultrasonic vibrations which characterizes the physical make-up of said object under test.

21. A system for detection of imperfections and measurement of properties of the internal portion of an object including
(a) a source of ultrasonic acoustic energy generating a wave mode which propogates along said object under test comprising
  (1) a signal generator,
  (2) a transmitter transducer located on one side of said object under test, said transmitter transducer having a surface from which said ultrasonic acoustic energy propogates disposed at an angle relative to the surface of said object, and
  (3) means forming a part of said transmitter transducer for optimizing the coupling efficiency of said ultrasonic acoustic energy into ambient air
(b) a reflective surface, said reflective surface supported near said transmitter transducer surface to reduce the diameter of said ultrasonic acoustic-energy propogating from said transmitter transducer, said reflective surface disposed at an angle of 90° relative to the surface of said object, and wherein said reflective surface is parabolic to direct said ultrasonic acoustic energy toward said surface of said object,
(c) a receiver transducer spaced from said object and coupled by ambient air with ultrasonic vibration emitted from said object, said receiver transducer located on the side of said object opposite said transmitter transducer,
(d) means comprised of at least first and second layers of material, each layer having an acoustic impedance, forming a part of said receiver transducer for matching acoustic impedance and optimizing the coupling efficiency of said emitted ultrasonic vibrations from ambient air into a piezoelectric material, and
(e) detector means for detecting any attenuation of the energy level of said emitted ultrasonic vibrations which characterizes the physical make-up of said object under test.

22. A transducer assembly for use in a system for detection of imperfections and measurement of properties of the internal portion of an object using ambient air to transmit ultrasound to, and receive ultrasonic vibrations emitted from the object, said transducer assembly including
(a) a piezoelectric material having capability of transforming oscillatory energy at a resonant frequency of the transducer assembly to ultrasonic energy and the reverse, and
(b) a first matching layer including two individual layers comprised of
  (1) a layer of plexiglass, and
  (2) a layer of aluminum, respectively,
(c) a second matching layer comprised of balsa wood disposed on the side of said matching layer further from said piezoelectric material, and wherein said first and second matching layers forming a part of said transducer assembly each having an acoustic impedance, said second matching layer only having a thickness equivalent to a quarter wavelength or multiple thereof, said first and second matching layers adapted for matching acoustic impedance and optimizing the coupling efficiency of said ultrasonic energy and airborne ultrasound into and from ambient air, and said airborne ultrasound which is adapted to be emitted from said object whose internal properties are subject to test being attenuated by any imperfection of property thereby bearing a relationship to the physical make-up of said object.

23. The transducer of claim 22 wherein said plexiglass layer is adjacent said piezoelectric material and said aluminum layer is adjacent said layer of balsa wood.

24. A transducer assembly for use in a system for detection of imperfections and measurement of properties of the internal portion of an object using ambient air to transmit ultrasound to, and receive ultrasonic vibrations emitted from the object, said transducer assembly including
(a) a piezoelectric material having capability of transforming oscillatory energy at a resonant frequency of the transducer assembly to ultrasonic energy and the reverse, and
(b) a first matching layer including two individual layers comprised of
  (1) a layer of plexiglass, and
  (2) a layer of steel, respectively,
(c) a second matching layer comprised of polystrene foam disposed on the side of said first matching layer further from said piezoelectric material, and wherein said first and second matching layers forming a part of said transducer assembly each have an acoustic impedance, said second matching layer only having a thickness equivalent to a quarter wavelength or multiple thereof, said first and second matching layers adapted for matching acoustic impedance and optimizing the coupling efficiency of said ultrasonic energy and airborne ultrasound into and from ambient air, and said airborne ultrasound which is adapted to be emitted from said object whose internal properties are subject to test being attenuated by any imperfection of property thereby bearing a relationship to the physical make-up of said object.

25. The transducer of claim 24 wherein said plexiglass layer is adjacent said piezoelectric material and said steel layer is adjacent said layer of polystyrene foam.

* * * * *